United States Patent [19]

Horie et al.

[11] Patent Number: 5,666,966
[45] Date of Patent: Sep. 16, 1997

[54] SUCTION-TYPE BLOOD SAMPLER

[75] Inventors: Masao Horie; Yoshikazu Kishigami, both of Ootsu; Hiroyuki Nakagami; Masayuki Takatera, both of Kusatsu, all of Japan

[73] Assignee: Nissho Corporation, Osaka, Japan

[21] Appl. No.: 459,962

[22] Filed: Jun. 2, 1995

[30] Foreign Application Priority Data

Jun. 24, 1994 [JP] Japan ................................ 6-166125

[51] Int. Cl.$^6$ ........................................................ A61B 5/00
[52] U.S. Cl. ................................................ 128/760; 128/770
[58] Field of Search ........................................ 128/763, 765, 128/770; 606/181, 182; 604/131

[56] References Cited

U.S. PATENT DOCUMENTS 5,350,392 9/1994 Purcell et al. ........................ 606/182
5,368,047 11/1994 Suzuki et al. ........................ 128/765

FOREIGN PATENT DOCUMENTS 0 554 995 A1 8/1993 European Pat. Off. .

*Primary Examiner*—Sam Rimell
*Assistant Examiner*—Pamela L. Wingood
*Attorney, Agent, or Firm*—Kubovcik & Kubovcik

[57] ABSTRACT

A suction-type blood sampler has a housing (1), a lancet unit (2) having a rod (4) extending backward from the lancet unit, and a plunger (3) connected to the rod in the housing and having a seal (7) attached to a forward end of the plunger. The seal is in sliding airtight contact with an inner periphery of the housing. The lancet unit consists of a lancet body (11) having a forwardly extending needle (12) and held by a lancet retainer (18) which is in sliding contact with the inner periphery. The blood sampler further has first, second and third springs (8, 9, 10) placed between the lancet unit and the plunger. The second spring urges the lancet unit to project the needle forwards, and the third spring tends to retract it. The first spring acts to reduce air pressure in the housing when the plunger is released. The blood sampler also has an air sealing means (32) disposed in the plunger so as to exhaust air and inhibit ambient air from entering the housing, so that the skin is pierced sharply and quickly, and by introducing ambient air into the evacuated housing, just a required amount of blood can be taken accurately and without any fear that the blood will scatter when the open end of the housing is removed from the skin.

5 Claims, 6 Drawing Sheets

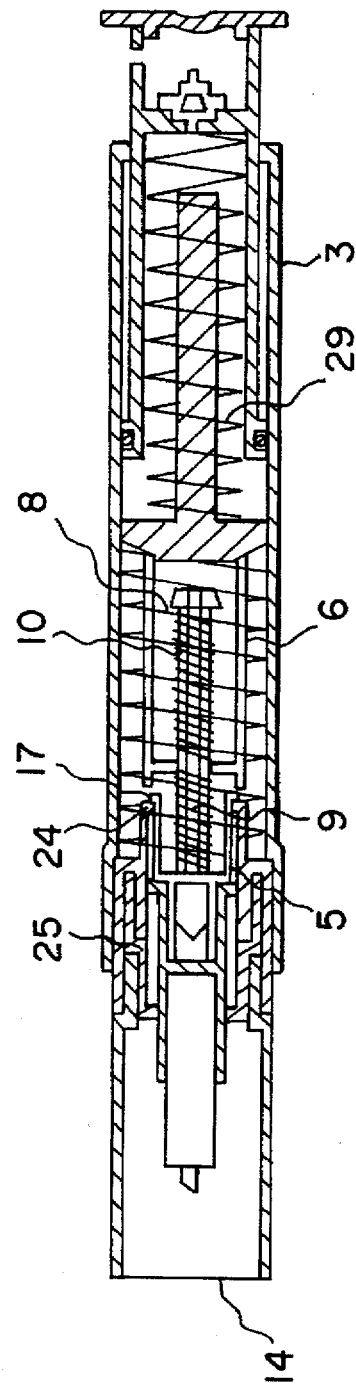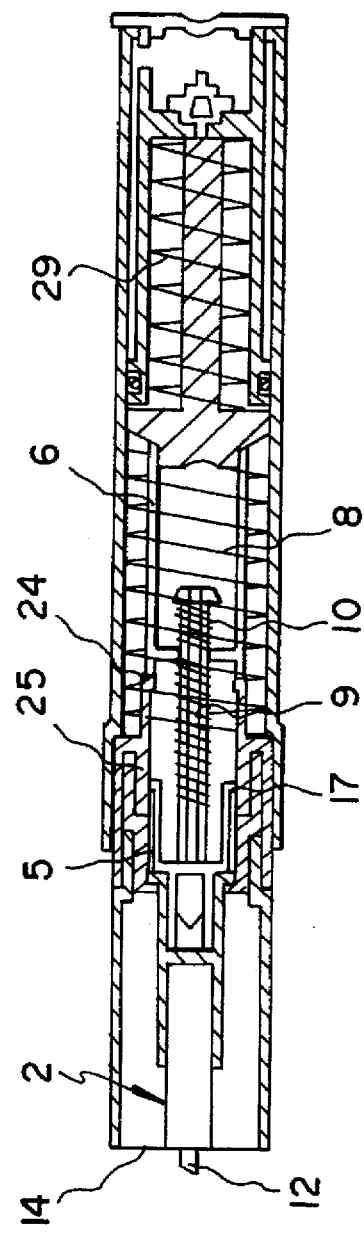

SUCTION-TYPE BLOOD SAMPLER

BACKGROUND OF THE INVENTION

1. Field of the Invention

The present invention relates to a blood sampler of the suction type useful for sampling from a human a necessary amount of blood to be subjected to various blood tests, by thrusting a needle into the skin of the human and applying a vacuum of a certain degree to the skin to draw the blood sample into the device.

2. Description of Prior Art

Each of the known so-called lancet injectors generally comprises a pressable end and a blade opposed thereto and having an acute end capable of piercing human skin. By gently striking the pressable end, the acute end will pierce, for example, the skin of a finger. A small amount of blood will ooze out of the skin to be taken into a container by using a pipette or the like and is then subjected to necessary tests. There are many fine blood vessels in a finger so that a finger can be pressed to cause a small drop of blood to ooze therefrom. Since fingers are more sensitive to pain, an upper arm, abdomen or thigh have recently been used for blood sampling. Similar devices are also used in the latter case, and an example thereof is disclosed in Japanese Patent Publication Kokai No. Sho-62-38140. This device comprises a cylindrical housing and a lancet support, which has a gasket or the like slidably accommodated in the housing. Springs will retract the lancet support to thereby reduce air pressure in the housing so that it sucks a blood sample automatically and immediately after a lancet pierces the skin.

The gasket in the prior art device fixed to the lancet support is in airtight contact with the inner peripheral surface of the housing. Friction between the gasket and the inner surface will lower the thrust speed of the lancet or needle, thereby increasing pain. Further, the lancet support is automatically held in place where the skin sticks to the device, due to the reduced air pressure. When the housing is taken off, the skin will spring back and ambient air will rush into the housing. In such a case, the oozed blood scatters and is lost, and an additional amount thereof is needed.

SUMMARY OF THE INVENTION

An object of the present invention is, therefore, to provide a blood sampler of the suction type that can pierce human skin at a higher speed when sampling a desired quantity of blood, and can break the reduced air pressure so that the blood is protected from scattering.

A blood sampler of the suction type provided herein comprises: a housing; a lancet unit accommodated in a front region of the housing; a rod extending backwardly from the lancet unit; a plunger accommodated in a rear region of the housing and having a seal attached to a forward end of the plunger; the seal being in sliding and airtight contact with an inner peripheral surface of the housing; the housing having an open frontal end and an open rearward end; the lancet unit consisting of a lancet body fixed to a lancet retainer, and the lancet body having a needle extending forward; the lancet retainer being in sliding contact with the inner peripheral surface of the housing; a first spring, a second spring and a third spring all accommodated in the housing and between the lancet unit and the plunger, wherein the second spring urges the lancet unit forward to cause the needle to jut from the frontal end of the housing, and the third spring urges the lancet unit to be retracted behind the frontal end, when the plunger is pressed, and wherein the first spring subsequently acts to reduce the air pressure in the housing, when the plunger is released; and further comprising a checking means disposed in a rear region of an internal cavity of the plunger and capable of exhausting air out of the housing, but inhibiting air from entering the housing through the internal cavity of said plunger.

The suction-type blood sampler can be designed such that the first spring intervenes between the lancet unit and the internal cavity of the plunger, and further comprises: an inner cylindrical member; a flange formed integral with a rear end of the rod; a spring separator; and a so-called hookable member fitted in a rear recess of the lancet unit, wherein the spring separator is formed around the rod and integral with the inner cylindrical member which extends forward from the plunger, and a second spring intervenes between the lancet unit and the spring separator, with a third spring being interposed between said spring separator and the flange, and wherein the hookable member is engageable with a rearward rim extending radially and inwardly from the inner peripheral surface of the housing.

The suction-type blood sampler may further comprise a fourth spring and a first partition, with the partition being attached to and closing a rear open end of the inner cylindrical member, so that the first spring is interposed between the lancet unit and the first partition, with the fourth spring being disposed partially in the internal cavity of the plunger and between the first partition and the rear region of said cavity.

The suction-type blood sampler can still further comprise a cap attached to the frontal end of the housing, and at least one lug formed in and integral with an inner periphery of the housing or cap, with the lug being behind the frontal end thereof so as to delimit the forward movement of the lancet unit.

The checking means in the suction-type blood sampler is preferably a check valve.

The suction-type blood sampler can further comprise a second partition for dividing the interior of the plunger into an internal cavity and a rear compartment disposed adjacent to and behind the internal cavity, wherein the second partition has a bore in which a check valve as the checking means is secured, and an air exhausting aperture is formed through a cylindrical wall defining the rear compartment.

The seal in the suction-type blood sampler can be an O-ring.

In operation of the blood sampler provided in a preferable embodiment (shown in FIG. 1), the frontal opening of the cap attached to the front end of housing will be pressed at first to the skin of a human. The plunger will then be pushed to move the inner cylindrical member forward until the front end thereof collides with the hookable member, while compressing the first and fourth springs. By continuing to push the plunger forward, the hookable member engages the rim extending from the forward portion of the inner peripheral surface of the housing, or extending from a basal portion of the cap attached to said housing, before the needle held by the lancet body pierces the human skin. The forward sliding movement of the hookable member within the forward region of said housing will be accompanied by the compression of the third spring. Upon the needle pricking the skin, this third spring will instantaneously expand. When the plunger is subsequently released, the first and fourth springs will repel the plunger backward. As a result, the internal spaces formed by the plunger and the housing whose forward opening is closed by means of contact with the human skin will be evacuated to cause the blood to be drawn out from the pricked pinhole of the human skin. By visually inspecting this process through a transparent front wall of the housing, the plunger can be pressed forward a little when the required amount of blood has been taken. Such a forward pressing of the plunger will decrease the volume of the internal spaces, thereby breaking the evacuated state thereof to smoothly remove the forward opening of the housing from the skin, without scattering the blood which has oozed from the skin.

BRIEF DESCRIPTION OF THE DRAWINGS

FIGS. 2 to 7 illustrate sequential steps, viz. first to sixth steps, in the operation of the blood sampler shown in FIG. 1, in which:

FIG. 2 is a cross-section showing the first step;

FIG. 3 is a cross-section showing the second step;

FIG. 4 is a cross-section showing the third step;

FIG. 5 is a cross-section showing the fourth step;

FIG. 6 is a cross-section showing the fifth step;

FIG. 7 is a cross-section showing the sixth step;

DETAILED DESCRIPTION OF THE PREFERRED EMBODIMENTS

Figure 1:
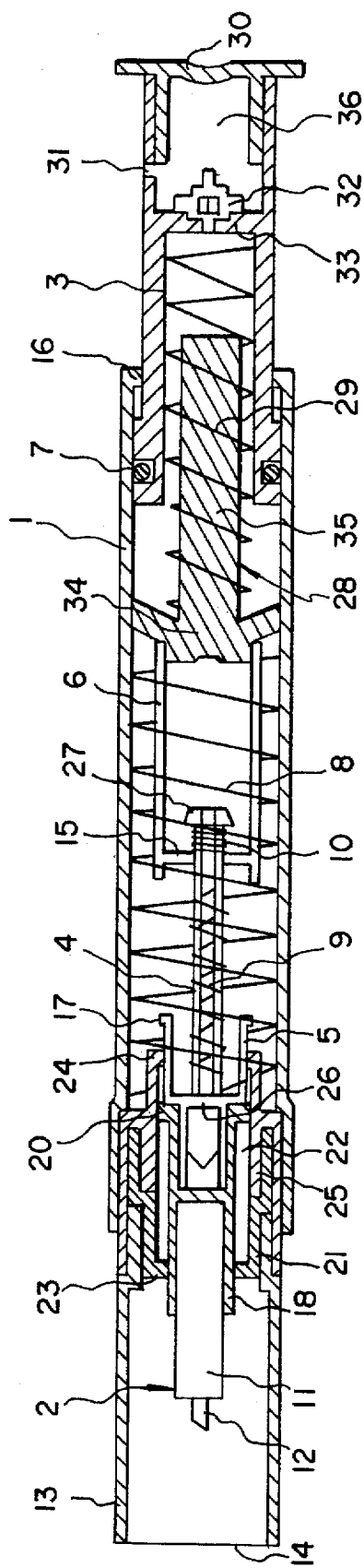
FIG. 1 is a cross-section of a suction-type blood sampler according to an embodiment of the invention.

A suction-type blood sampler of the embodiment shown in FIG. 1 comprises a cylindrical cap 13 fitted on a frontal end of a housing 1. A lancet body 11 held by a lancet retainer 18 has a needle 12 to be used for piercing human skin. A lancet unit 2 consists of the lancet body 11 and the lancet retainer 18, in which a hookable member 5 fits. An annular lug 20 protrudes radially and outwardly from the rear end of the lancet retainer 18. A forward sheath 21 having a forward rim 23 is secured to the inner periphery of the forward region of housing 1. A rearward sheath 25 extending rearward from the forward sheath is flush therewith and has a rearward rim 24. Both the rims 23 and 24 protrude radially and inwardly, so that a cylindrical clearance 22 is formed between the hookable member, lancet retainer and the sheaths. The annular lug 20 of the lancet retainer is capable of reciprocating between the rims 23 and 24. A rearward lug 17 of the hookable member 5 is normally and temporarily prevented from moving forward beyond the rearward rim 24. The forward sheath 21 serves as a member to always prevent the lancet retainer from moving forward beyond its forwardmost position, while the rearward sheath 25 serves as a member for always preventing the lancet retainer from being retracted beyond its rearwardmost position. On the other hand, however, the rearward lug 17 can be forced reversibly by the relevant springs to move fore and aft beyond the rearward rim 24, so that the hookable member 5 can slide within the cylindrical clearance 22.

Cap 13 is attached to the frontal end of the housing 1, so that the needle 12 is normally accommodated in the cap 13 to protect the human skin from being accidentally pricked. The cap 13 is preferably transparent to enable a visual determination as to whether the required amount of blood sample has or has not been taken. The lancet body 12 can be replaced with a new one before taking the next blood sample. At least one lug 19 is formed in and integral with an inner periphery of cap 13 serving as a front extension of the housing.

A thin rod 4 extends rearwardly from a central portion of a bottom 26 of the hookable member 5, through a bore of a spring separator 15, and into an inner cylindrical member 6. Secured to a rear end of the rod 4 is an end of a third coil spring 10. A flange 27 integral with the rear end of the rod prevents the third spring from being retracted beyond said rod 4. A second coil spring 9 and the third spring 10 always surround the rod 4. In detail, the second spring 9 is retained between the bottom 26 of the hookable member 5 and the spring separator 15. When plunger 3 is urged forward in use, the second spring 9 will be compressed until the rearward lug 17 of the hookable member 5 disengages from the rearward rim 24 of the rearward sheath 25. Thus the hookable member will be allowed to advance further forward, whereby the lancet retainer 18 and the lancet body 11 will spring forward to cause the needle 12 to prick the human skin. The third spring 10 disposed between the spring separator 15 and the flange 27 of the rod 4 will act subsequently to retract the needle 12 rearwardly beyond the opening 14 and restore the needle into the housing 1, after the needle pricks the human skin. At the time the needle 12 pricks the human skin, the inertial forward movement of the rod 4 compresses the third spring 10 and, as a reaction to this inertial displacement, causes this spring to expand. Thus, the needle will spring back into the cap 13 through its opening 14.

Extended forward from a first partition 34 integral with a forward end of a thick rod is an inner cylindrical member 6 having the spring separator 15 fixed to a forward end thereof. The forward extremity of the cylindrical member 6 is adapted to abut against the rearward lug 17 of the hookable member 5, when the plunger 3 urges the first partition 34 forward. A further forward movement of the plunger will cause the forward end of the cylindrical member 6 to force the hookable member 5 forward. The plunger 3 is slidable along the inner periphery of the housing 1, always forward of a rear end lug 16 thereof. A seal 7 attached to the outer periphery of a frontal end of said plunger 3 keeps the interior of the housing 1 airtight. The seal 7 can be made of a metal, or more desirably an O-ring or like packing made of an elastomer such as a rubber, in order to reduce the friction between the housing and the plunger 3. Thus, the seal 7 kept in airtight sliding contact with the inner periphery of the housing 1 will inhibit the air normally present in the housing 1 from being exhausted, and will also prevent ambient air from entering the housing when the housing is in an evacuated state.

Figure 8:
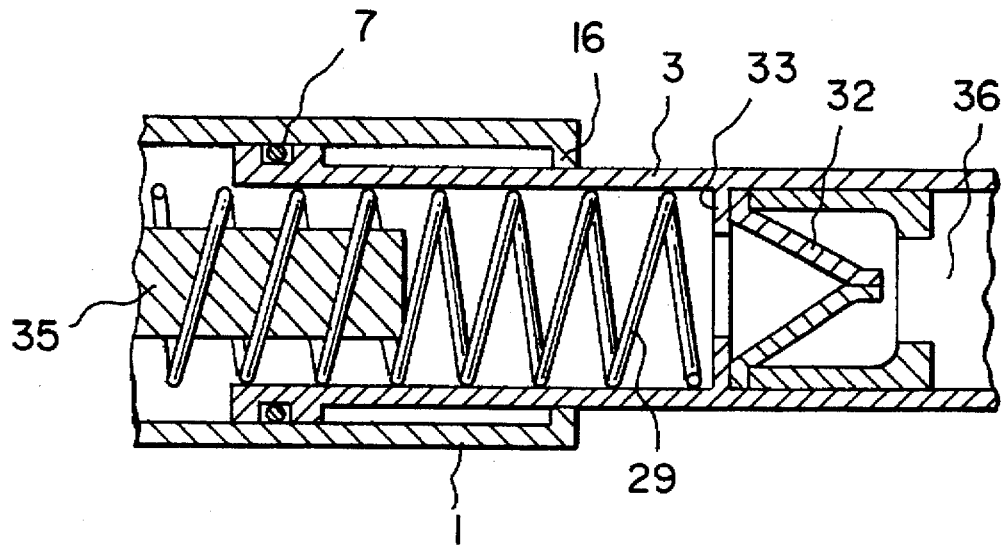
FIG. 8 is an enlarged cross-section of a checking means and relevant members adjacent thereto and employed in the blood sampler shown in FIG. 1.

FIG. 8 illustrates in cross-section the O-ring employed as the seal 7 in this embodiment. The O-ring carried by the frontal end of the plunger 3 will bear against the rear end lug 16 of the housing 1 in such a manner that the plunger is protected from slipping off. Referring again to FIG. 1, a partitioning means 28 consists of the first partition 34 and a thick rod 35 formed integral therewith and extending rearward therefrom and coaxially therewith. The first partition 34 is in a sliding contact with the inner periphery of the housing 1. A fourth coil spring 29 is interposed between the first partition 34 and a second partition 33 formed integral with and proximal to the rear end of the plunger. When the plunger 3 is pressed forwards, the fourth spring 29 is compressed and, if the first spring 8 is of insufficient elastic force, it is compressed by the compressed power of the fourth spring 29. In another case wherein the fourth spring 29 is dispensed with and the first spring 8 extends between the lancet unit 2 and the second partition 33, the partitioning means 28 may be dispensed with.

A check valve means is disposed in a rear region of an internal cavity of the plunger 3. This check valve means is capable of exhausting air out of the housing 1, but prevents air from entering the housing through the internal cavity of said plunger. In the embodiment shown in FIG. 1, a check valve 32 is employed as the checking means and is attached to the second partition 33. The second partition 33 divides the interior of the plunger 3 into an internal cavity and a rear compartment 36 disposed adjacent to and behind the internal cavity. An air exhausting aperture 31 is formed through a cylindrical wall defining the rear compartment. The check valve 32, which is duck-bill shaped as shown in FIG. 8, permits the pressurized air present in the closed space defined by the housing 1, the plunger 3 and the human skin to be relieved through the rear compartment 36 when the plunger 3 is pressed forwards. The check valve need not necessarily be a duck-bill valve, and can be a bevel valve, a flap valve, a poppet valve or a ball valve.

Figure 9:
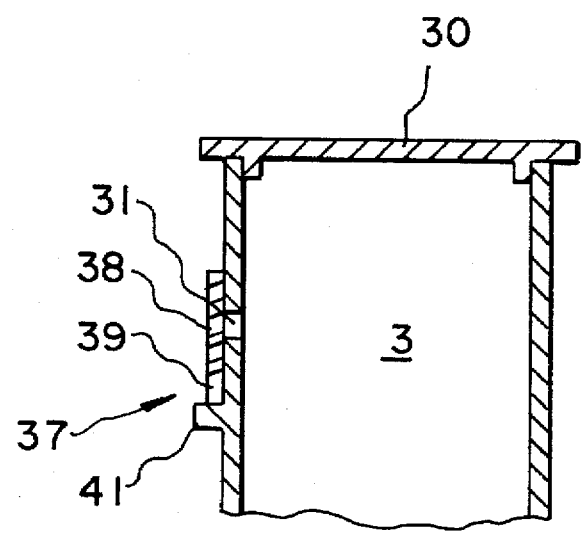
FIG. 9 is a cross-section of a modified air sealing means which allows internal air to be exhausted from the housing, but inhibits ambient air from entering the housing through its rear end.

A modified example of the checking means is illustrated in FIG. 9, in which said means comprises a lid 37 openably closing the aperture 31 shown in FIG. 1. This lid 37 is composed of an outer rigid plate 39 and an inner elastic sheet 38 bonded thereto. The rigid plate has a basal end secured to an outer protrusion 41 jutting sideways from the outer periphery of the plunger 3. The lid 37 will remain closed during the backward movement of the plunger so as to keep the interior evacuated, but will open when the plunge is advanced forwards.

In use, the suction-type blood sampler will follow the sequential steps as shown in FIGS. 2 to 7. In the first step shown in FIG. 2, the first and fourth springs 8 and 29 are in their expanded state and the lancet retainer 18 takes its rearwardmost position, but is exposed to the outside. The second spring 9 is in its expanded state, with the third spring 10 being compressed. The lancet body 11 of the lancet unit 2 will be set in the lancet retainer 18 of the blood sampler in this state. Subsequently, the transparent cap 13 is attached to the frontal end of the housing 1, so as to enclose the needle 12 with the cap as shown in FIG. 1. In the case illustrated in FIGS. 1 and 2, the lancet body 11 is renewed. However, the blood sampler can be discarded as a whole, once it is used. In this case, the housing 1 can be molded integrally with the cap 13 so that the lug 19 is located close to but behind the frontal end of such a housing.

Figure 2:
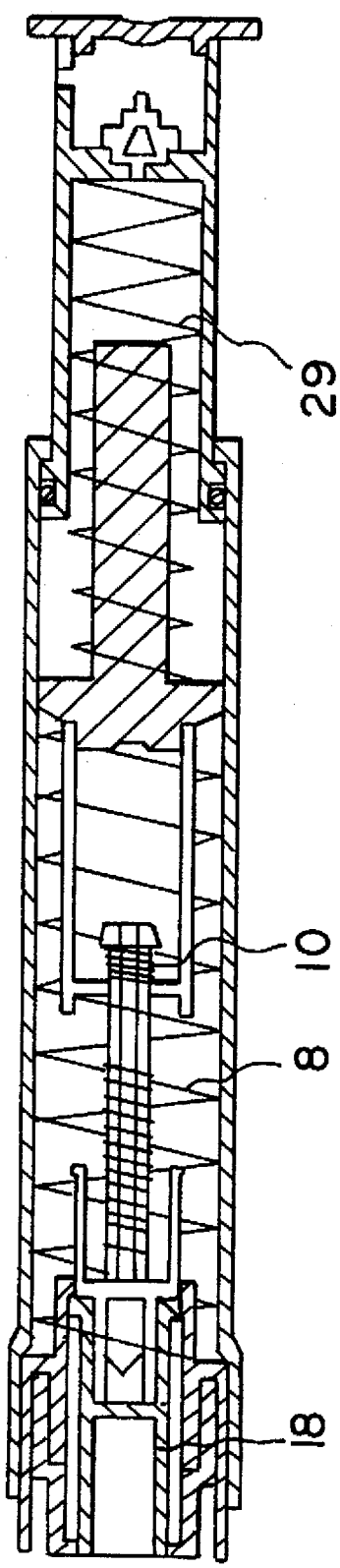
Figure 3:
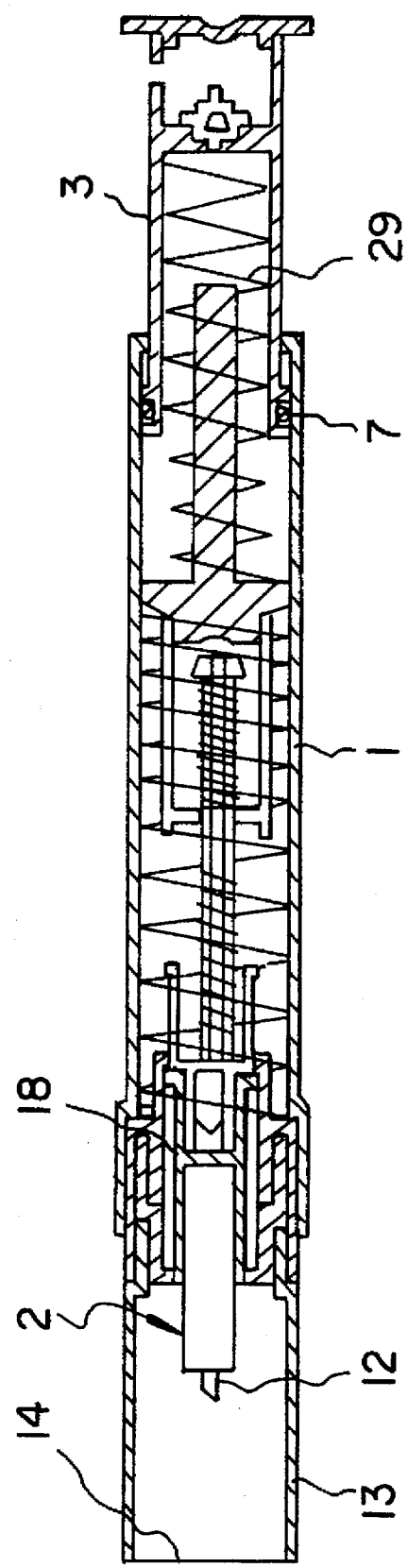

In the second step, the plunger 3 will be driven forwards a certain distance to move forwards the inner cylindrical member 6 as shown in FIG. 3. The first, second and fourth springs 8, 9 and 29 are thus compressed a little, as compared with their state as shown in FIG. 2, though the third spring 10 is expanded. The opening 14 of the housing 1 may be pressed to the human skin, after or before the blood sampler is brought into the state shown in FIG. 3. A strong pressure, which the opening 14 applied to the human skin will impart to the portion thereof to be pricked, will divert a patient's or user's mind from the pain when the needle 12 pricks his or her skin. In the third step, the plunger 3 will be urged further forwards, until the inner cylindrical member 6 collides with the rearward lug 17 of the hookable member 5 as shown in FIG. 4. The second spring 9 is further compressed, as compared with the state shown in FIG. 3, with the third spring 10 being further expanded.

Figure 6:
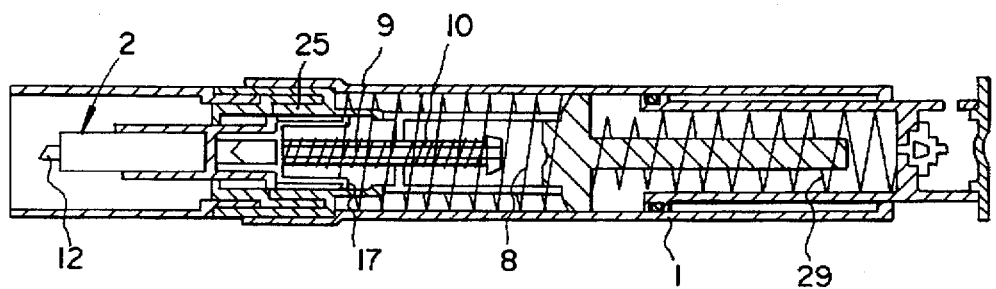

The plunger of the blood sampler shown in FIG. 4 is further pressed towards the human skin so that the front end of cylindrical member 6 will force the lug 17 of hookable member 5 to snap over the rearward rim 24. Thus, the lug 17 is allowed to slide along the inner periphery of the rearward sheath 25, whereby the second spring 9 which has been compressed will expand and force the lancet unit 2 forwards. The needle 12 thus projects forward through the opening 14 to instantaneously prick the human skin, as will be seen in FIG. 5 illustrating the fourth step, and simultaneously the third spring 10 which has been expanded will be quickly compressed. The third spring 10 compressed temporarily in this manner will expand again, once the needle 12 pricks the human skin. As a result, the lancet unit 2 is retracted and the needle 12 thereof returns into the housing 1, with the lug 17 still sliding along the rearward sheath 25 as shown in FIG. 6 illustrating the fifth step.

Figure 7:
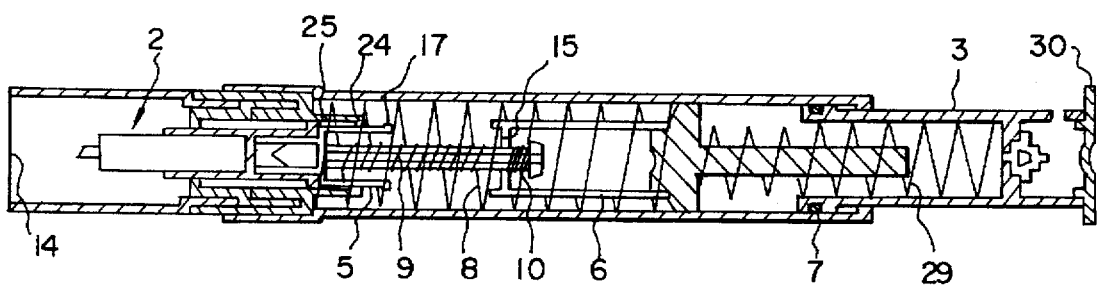

Next, the plunger 3 will move backwards while the opening 14 of housing 1 is continued to be pressed against the human skin. Although the plunger 3 may be pulled manually, it may be caused to spontaneously make such a backward movement by the expansion of the compressed first and fourth springs 8 and 29. For such a spontaneous retraction, the operator need only to disengage his or her finger from the rear end plate 30 of the plunger. Thanks to the elastic force of the first and fourth springs 8 and 29 which have been compressed and then tend to expand, the blood sampler will thus take a position shown in FIG. 7 illustrating the sixth step of the operation. The lid 37 shown in FIG. 9 will remain closed during this process of using the blood sampler. Consequently, the lug 17 sliding along the rearward sheath 25 will return into the housing 1 beyond the rearward rim 24, since the spring separator 15 integral with the cylindrical member 6 moves backward to retract the rod 4 integral with the hookable member 5. Because the seal 7 is in airtight contact with the housing's inner periphery and the opening 14 is still pressed to the human skin, the plunger 3 moving backward will decrease the air pressure in the closed interior of the housing. Due to such an evacuated state of the housing 1, the blood sample will be drawn from the skin portion pricked with the needle. Upon visual detection of a required amount of oozed sample blood, the plunger 3 can be pressed forward to increase the pressure in the closed space of housing and plunger, to thereby break the evacuated state thereof. Thus, the opening 14 of the blood sampler can be removed from the human skin, without scattering the oozed blood.

In summary, the suction-type blood sampler provided in this invention has a needle which can very quickly pierce the human skin. Therefore, no sharp pain will be felt by people from whom the blood samples are taken. Blood sampling is possible even if the density of fine blood vessels is low in the skin portion, because the blood oozing from the skin portion pierced with the needle is sucked or drawn from the skin. By introducing ambient air easily into the housing to compensate for the evacuation thereof, only a required amount of blood can be drawn accurately and without any fear that the blood will scatter when the open end of the housing is removed from the skin.

What is claimed is:

1. A suction-type blood sampler comprising:
   a housing, the housing having an open frontal end and an open rearward end;
   a lancet unit accommodated in a front region of the housing, the lancet unit comprising a lancet body fixed to a lancet retainer, the lancet body having a needle extending forward toward the frontal end of the housing and the lancet retainer being in sliding contact with the inner peripheral surface of the housing;

a rod attached to and extending backward from the lancet unit toward the open rearward end of the housing;

a plunger provided in a rear region of the housing and having a seal attached to a forward end of the plunger, the seal being in sliding and airtight contact with an inner peripheral surface of the housing;

an inner cylindrical member which extends forward of the plunger;

a flange formed integral with a rear end of the rod;

a spring separator formed around the rod and integral with the inner cylindrical member;

a hookable member fitting in a rear recess of the lancet unit, the hookable member being engageable with a rearward rim extending radially and inwardly from the inner peripheral surface of the housing;

a first partition attached to and closing a rear open end of the inner cylindrical member;

a first spring, a second spring and a third spring all accommodated in the housing between the lancet unit and the plunger, wherein the second spring intervenes between the lancet unit and the spring separator and urges the lancet unit forward to move the needle outwardly of the frontal end of the housing, and the third spring is interposed between the spring separator and the flange and urges the lancet unit to be retracted behind the frontal end, when the plunger is pressed, and wherein the first spring is interposed between the lancet unit and the first partition and urges said plunger to move toward said open rearward end and to reduce the air pressure in the housing, when the plunger is released;

a fourth spring disposed partially in an internal cavity of the plunger and between the first partition and the rear region of said cavity; and an air sealing means disposed in a rear region of an internal cavity of the plunger for exhausting air out of the housing, but inhibiting air from entering the housing through the internal cavity of said plunger.

2. The suction-type blood sampler as defined in claim 1, further comprising a cap attached to the frontal end of the housing, and at least one lug formed in and integral with an inner periphery of the cap, with the lug being behind a frontal end thereof so as to delimit the forward movement of the lancet unit.

3. The suction-type blood sampler as defined in claim 1 or 2, wherein the air sealing means is a check valve.

4. The suction-type blood sampler as defined in claim 1 or 2, further comprising a second partition for dividing the interior of the plunger into the internal cavity and a rear compartment disposed adjacent to and behind the internal cavity, wherein the second partition has a bore in which a check valve as the air sealing means is secured, and an air exhausting aperture is formed through a cylindrical wall defining the rear compartment.

5. The suction-type blood sampler as defined in claim 1, wherein the seal is an O-ring.

\* \* \* \* \*